United States Patent [19]

Belkin

[11] Patent Number: 5,733,276
[45] Date of Patent: Mar. 31, 1998

[54] METHOD FOR PROPHYLACTIC THERAPY FOR POST-OPERATIVE POSTERIOR CAPSULAR OPACIFICATION

[75] Inventor: Michael Belkin, Givat Shmuel, Israel

[73] Assignee: Ramot University Authority for Applied Research & Industrial Development Ltd., Tel-Aviv, Israel

[21] Appl. No.: 700,242

[22] Filed: Aug. 20, 1996

[51] Int. Cl.⁶ .................................... A61B 17/36
[52] U.S. Cl. ............................................ 606/6
[58] Field of Search ................ 606/4, 5, 6, 10, 606/11, 12

[56] References Cited

U.S. PATENT DOCUMENTS

| | | |
|---|---|---|
| 4,538,608 | 9/1985 | L'Esperance, Jr. |
| 4,825,865 | 5/1989 | Zelman .................... 606/6 |
| 5,257,988 | 11/1993 | L'Esperance, Jr. ........... 606/6 |
| 5,263,950 | 11/1993 | L'Esperance, Jr. ........... 606/6 |
| 5,445,636 | 8/1995 | Bretton .................. 606/6 X |
| 5,445,637 | 8/1995 | Bretton ................... 606/41 |

*Primary Examiner*—Jennifer Bahr
*Assistant Examiner*—Sonya Hans-Ogugua
*Attorney, Agent, or Firm*—Helfgott & Karas, P.C.

[57] ABSTRACT

A method for prophylactic therapy for post-cataract extraction posterior capsular opacification of an eye having a lens posterior capsule, the method including the step of irradiating the lens capsule with laser radiation so as to destroy cells which remain in the lens capsule after extraction of the cataract, the laser radiation being substantially absorbable in water and of a level less than that required to rupture the lens capsule.

3 Claims, 1 Drawing Sheet

METHOD FOR PROPHYLACTIC THERAPY FOR POST-OPERATIVE POSTERIOR CAPSULAR OPACIFICATION

FIELD OF THE INVENTION

The present invention relates to methods for ophthalmic surgery generally, and particularly to methods for prophylactic therapy for post-operative posterior capsular opacification.

BACKGROUND OF THE INVENTION

The most common complication of modern cataract surgery, whether performed by extracapsular cataract extraction or by phacoemulsification, is posterior capsular opacification (PCO). PCO is the formation of a fibrotic membrane behind the artificial intraocular lens (IOL) implanted during the operation. This condition occurs in more than half the patients within five years of surgery (American Academy of Ophthalmology, Basic and Clinical Sciences Course, 1986–1989, Vol. 8 p.142). The fibrotic membrane leads to blur, glare and light reflections. When the membrane encroaches on the visual axis, it gradually reduces visual acuity down to blindness. This condition is caused by the persistence of lens cells in the lens capsule after the cataract has been removed. The modern treatment of this condition is neodymium:YAG laser photodisruption of the opacified posterior lens capsule. This relatively simple and effective procedure carries, however, quite a few serious risks, inter alia:

1. Elevation of the intraocular pressure, which in some cases leads to glaucoma.
2. Pitting and cracking of the intraocular lens.
3. Rupture of the anterior hyaloid face which may lead to forward movement of the vitreous and thus to secondary pupillary block and glaucoma and late onset corneal swelling and opacity.
4. Retinal detachment.

These problems and the inconvenience to patients due to declining vision and the necessity of extra procedures, make a search for a prophylactic therapy for post-operative posterior capsular opacification important.

SUMMARY OF THE INVENTION

The present invention seeks to provide a novel and efficient method for prophylactic therapy for post-operative posterior capsular opacification.

In the present invention, after removal of the cortex and nucleus of the cataract, the infrared energy of a laser whose irradiation absorbs well in water, is used to destroy any cells remaining in the posterior and anterior lens capsule and equator. Such a laser may be a carbon dioxide, erbium or holmium laser, for example. Good water absorption of the laser radiation is required in order to ensure that the beam will not pass through the transparent capsule and harm deeper eye structures such as the retina. The irradiation to be used should be of sufficient energy to destroy the cells but less than the level required to rupture the capsule.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
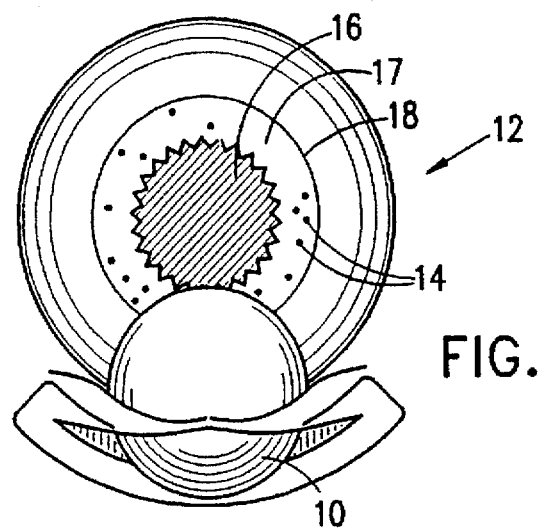
FIG. 1 is a simplified illustration of removing a cataract from an eye.

Reference is now made to FIG. 1 which illustrates removing an opacified lens 10 from an eye 12. In FIG. 1, the lens 10 is shown being removed by full incision extracapsular extraction, although it is appreciated that any other method for cataract extraction may be employed. After removing a cortex and nucleus of lens 10, a plurality of cells 14 generally remain in the posterior lens capsule 16, anterior lens capsule 17 and/or equator 18. It is a goal of the present invention to destroy cells 14 so as to prevent their causing PCO.

Figure 2:
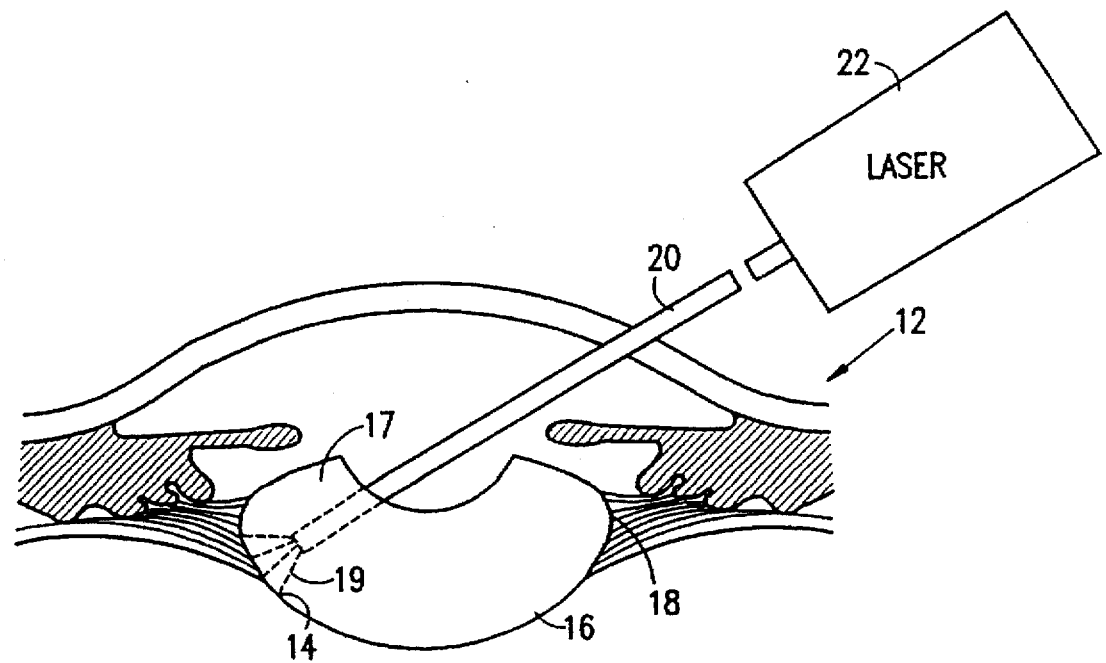
FIG. 2 is simplified illustration of a method for prophylactic therapy for post-cataract extraction posterior capsular opacification (PCO) of an eye, in accordance with a preferred embodiment of the present invention.

Reference is now made to FIG. 2 which illustrates a method for prophylactic therapy for post-cataract extraction PCO, in accordance with a preferred embodiment of the present invention. The lens capsule, including any or all portions of the posterior lens capsule 16, anterior lens capsule 17 and the capsule's equator 18, is irradiated with laser radiation 19 so as to destroy cells 14. Laser radiation 19 preferably absorbs well in water and is of a level less than that required to rupture the lens capsule. Preferably at least a portion of the periphery of the lens capsule, including the posterior lens capsule 16, anterior lens capsule 17 and equator 18, is irradiated with laser radiation 19, and the entire periphery may be irradiated.

Laser radiation 19 may be provided by a probe 20 which is connected to a laser 22 which provides radiation with good water absorption. Laser 22 may be a carbon dioxide, erbium or holmium laser, for example.

It will be appreciated by persons skilled in the art that the present invention is not limited to what has been particularly shown and described hereinabove. Rather, the scope of the present invention is defined only by the claims that follow:

What is claimed is:

1. A method for prophylactic therapy for post-cataract extraction posterior capsular opacification of an eye having a lens capsule, the method comprising the step of:

irradiating the lens capsule with laser radiation so as to destroy cells which remain in the lens capsule after extraction of the cataract, said laser radiation being substantially absorbable in water and of a level less than that required to rupture the lens capsule.

2. The method according to claim 1 and wherein said step of irradiating comprises irradiating at least a portion of the periphery of the lens capsule.

3. The method according to claim 1 wherein said radiation is provided by a laser selected from the group consisting of carbon dioxide, erbium and holmium laser.

* * * * *